(12) United States Patent
Kambara et al.

(10) Patent No.: US 7,670,992 B2
(45) Date of Patent: Mar. 2, 2010

(54) METHOD OF PRODUCING PROBE ARRAYS FOR BIOLOGICAL MATERIALS USING FINE PARTICLES

(75) Inventors: Hideki Kambara, Hachiouji (JP); Masato Mitsuhashi, Irvine, CA (US)

(73) Assignees: Hitachi Chemical Co., Ltd., Tokyo (JP); Hitachi, Ltd., Tokyo (JP); Hitachi Chemical Research Center, Inc., Irvine, CA (US)

( * ) Notice: Subject to any disclaimer, the term of this patent is extended or adjusted under 35 U.S.C. 154(b) by 334 days.

(21) Appl. No.: 11/484,046

(22) Filed: Jul. 10, 2006

(65) Prior Publication Data

US 2006/0275818 A1    Dec. 7, 2006

Related U.S. Application Data

(62) Division of application No. 10/964,602, filed on Oct. 12, 2004, now abandoned, which is a division of application No. 09/937,105, filed as application No. PCT/US00/09685 on Apr. 11, 2000, now abandoned.

(60) Provisional application No. 60/128,861, filed on Apr. 12, 1999.

(51) Int. Cl.
  *C40B 40/00*   (2006.01)
  *G01N 33/543*  (2006.01)
  *G01N 33/551*  (2006.01)
  *G01N 33/544*  (2006.01)

(52) U.S. Cl. .................. 506/13; 436/523; 436/524; 436/528

(58) Field of Classification Search .............. 506/13; 436/523, 524, 528
See application file for complete search history.

(56) References Cited

U.S. PATENT DOCUMENTS

| 5,585,275 A | 12/1996 | Hudson et al. |
| 5,804,384 A | 9/1998 | Muller et al. |
| 5,885,275 A | 3/1999 | Muller |
| 5,922,617 A | 7/1999 | Wang et al. |
| 6,214,560 B1 | 4/2001 | Yguerabide et al. |
| 6,288,220 B1 * | 9/2001 | Kambara et al. ......... 536/24.31 |
| 6,327,410 B1 * | 12/2001 | Walt et al. .................. 385/115 |
| 6,432,719 B1 | 8/2002 | Vann et al. |
| 6,872,535 B2 | 3/2005 | Baum |

FOREIGN PATENT DOCUMENTS

| EP | 0 723 149 A2 | 7/1996 |
| JP | 10-160705 | 6/1998 |
| WO | WO 98/53300 | 11/1998 |
| WO | WO 99/09042 | 2/1999 |
| WO | WO 99/32654 | 7/1999 |

OTHER PUBLICATIONS

Mitsuhashi et al. "Gene manipulation on plastic plates" *Nature* (1992) 357: 519-520.
Kozal et al. "Extensive polymorphisms observed in HIV-1 clade B protease gene using high-density oligonucleotide arrays" *Nature Medicine* (1996) 2:753-759.
Marshall et al. "DNA chips: an array of possibilities" *Nature Biotechnology* (1998) 16:27-31.
Kambara, H. Database HCAPLUS on STN Express, America Chemical Society, (Washington, D.C.) AN: 1999-684433, "Recent progress in fluorescent DNA analyzers and methods" abstract, *Curr. Top. Anal. Chem.* (1998) 1:21-36.

\* cited by examiner

*Primary Examiner*—Amber D. Steele
(74) *Attorney, Agent, or Firm*—Knobbe Martens Olson & Bear, LLP

(57) ABSTRACT

The use of probe arrays in which probes of various biological substances such as DNA are immobilized on the surface of a solid is becoming established as an effective means for high-speed screening. Different kinds of probes, such as DNA, are immobilized on the surface of a multiple number of independently treatable fine particles, such as beads, instead of the surface of a single solid, and the resulting beads are aligned in a capillary or a cell in a designated order. The size of the area where one probe is immobilized is reduced. The bead probe array is characterized in that such small beads are aligned one by one in a designated manner using a sheet with holes, and one or a multiple number of beads are held in the holes and then transferred to a probe array holder such as a capillary.

10 Claims, 11 Drawing Sheets

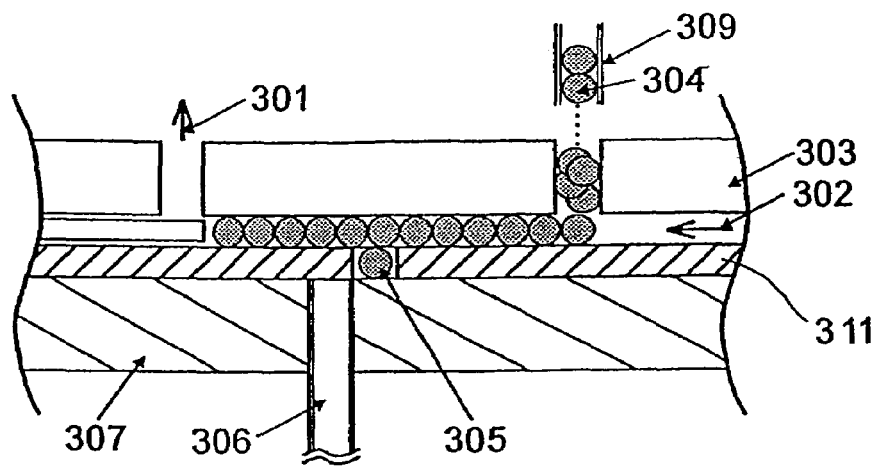
FIG. 3.a
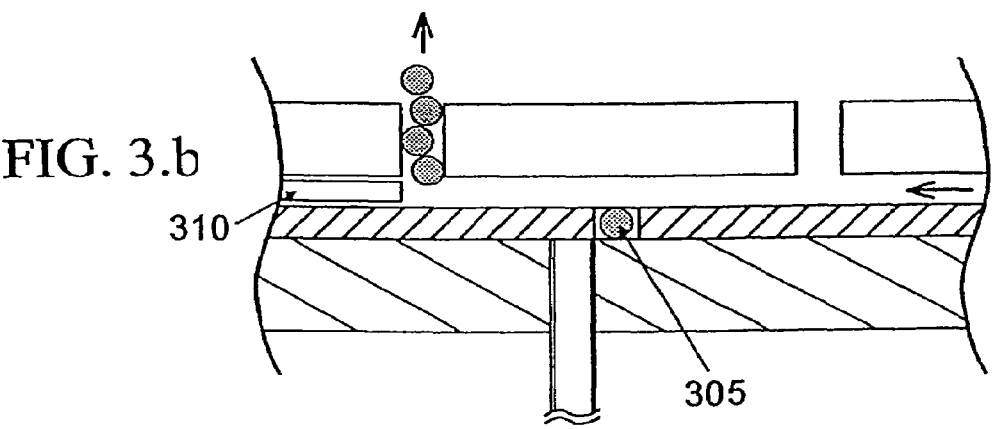
FIG. 3.b
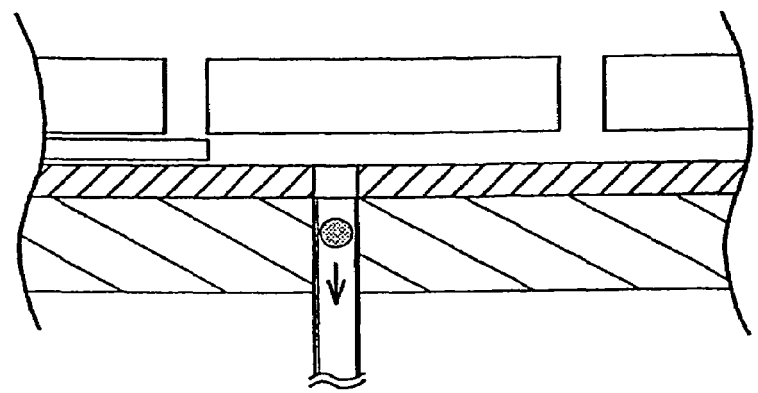
FIG. 3.c

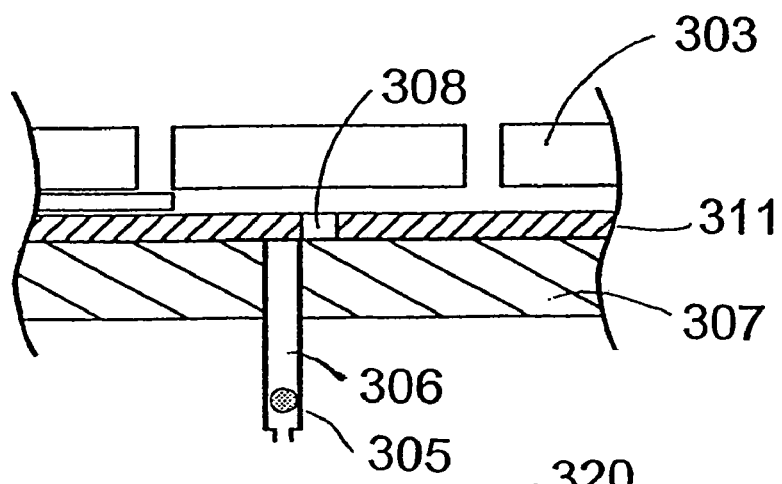
FIG. 3.d
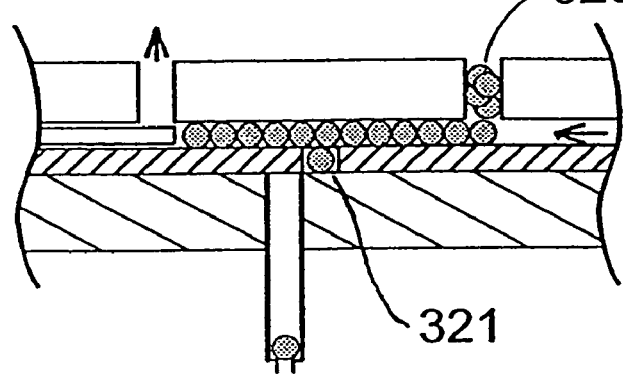
FIG. 3.e
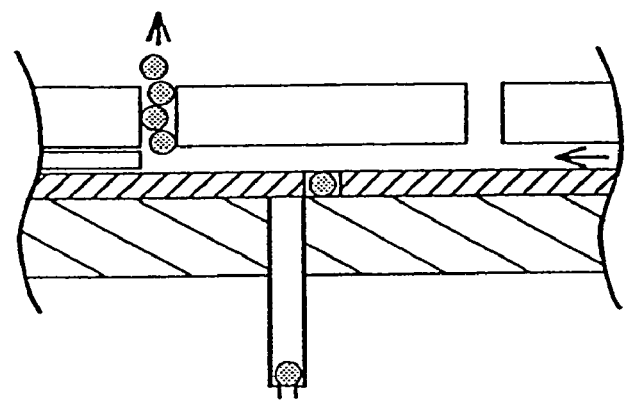
FIG. 3.f
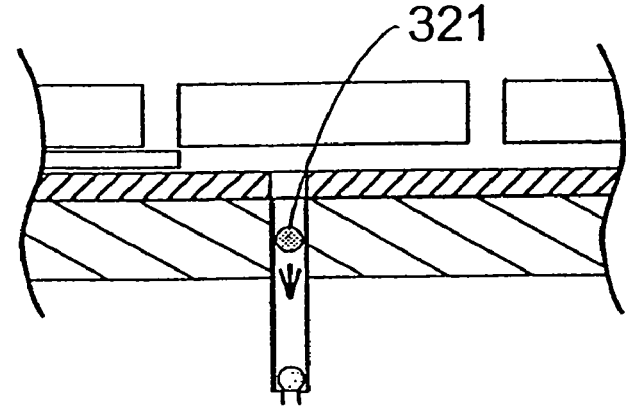
FIG. 3.g

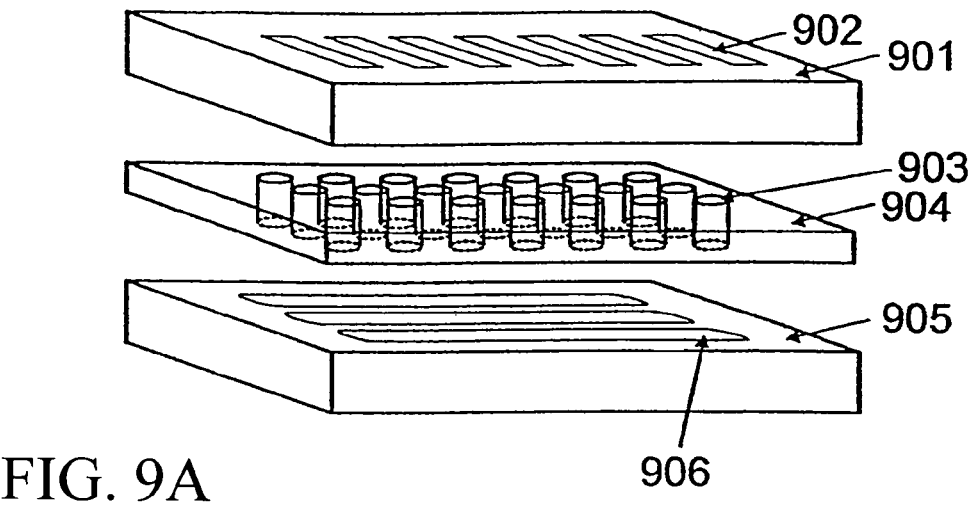
FIG. 9A
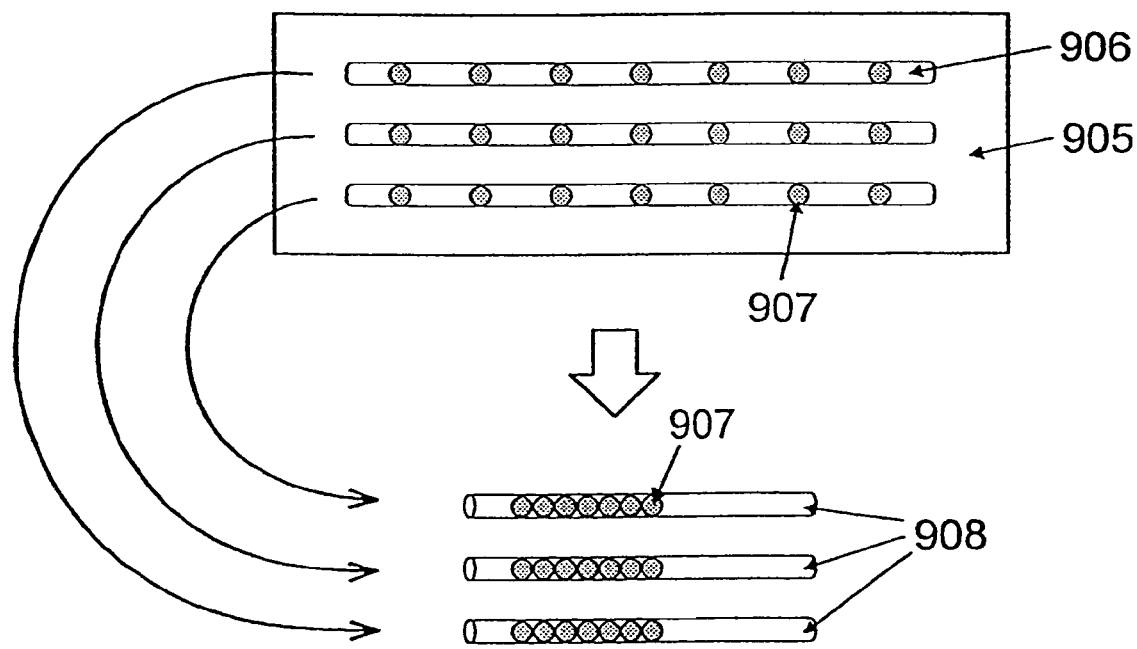
FIG. 9B
FIG. 9

METHOD OF PRODUCING PROBE ARRAYS FOR BIOLOGICAL MATERIALS USING FINE PARTICLES

RELATED APPLICATIONS

This application is a divisional of U.S. application Ser. No. 10/964,602, filed Oct. 12, 2004, now abandoned which is a divisional of U.S. application Ser. No. 09/937,105, filed Feb. 6, 2002, now abandoned which is a U.S. National Phase of International Application No. PCT/US00/09685 filed Apr. 11, 2000, which claims the benefit of priority of U.S. Provisional Application No. 60/128,861 filed Apr. 12, 1999, which is hereby expressly incorporated by reference in its entirety.

BACKGROUND OF THE INVENTION

1. Field of the Invention

The present invention relates to probe arrays for use in detecting peptides, proteins and DNAs, diagnosing, and analyzing biological materials including DNAs; and methods and apparatuses to produce the same.

2. Description of the Related Art

For DNA analyses or DNA tests or diagnoses, amplification of a small amount of DNA, isolation and identification of the amplified DNA fragments, and other procedures are necessary. For DNA amplification, PCR (polymerase chain reaction) is widely used, in which an extremely small number of DNAs can be multiplied by several orders of magnitude so as to be detectable. On the other hand, for the isolation and detection of different DNAs, among other methods, a DNA sequencer and fragment analyzer, in which gel electrophoresis and fluorescence detection are combined, are used. However, electrophoresis becomes very labor-intensive as the number of samples or test items increases. Thus, a simple method using DNA probes is drawing attention, in particular, a DNA chip, in which many kinds of probes are immobilized on the surface of a solid to make a probe array which undergoes hybridization with the sample, then only specific DNAs are trapped on the surface of the solid and detected (Nature Medicine 2, 753, 1996).

The probe detection method is used also for the analysis of proteins or peptides or various biological materials which interact with them, and a peptide chip corresponding to the DNA chip is now being used. This kind of isolation and detection method, in which a peptide or DNA is immobilized on the surface of a solid and hybridization proceeds between the peptide or DNA and a sample, has long been known as a blotting method in which the presence of the target DNA or the like is detected by a probe immobilized on a membrane using radioactive labeling. However, the DNA chip, on which a large number of probes can be immobilized on a small area (1 $cm^2$) of the surface of a solid such as glass or silicone, has the advantage in that only a small amount of sample is required, and a vast variety of probes can be used simultaneously. Methods for the production of DNA chips are divided broadly into two groups. In the first group, a DNA probe is synthesized one base at a time by a photochemical reaction on small segments (0.05 $mm^2$ to 0.2 $mm^2$) of a solid using the same photomasking technique as used for semiconductors or the like (Science 251, 767, 1991). In the second group, a synthesized DNA, PCR-amplified DNA, or DNA obtained by cloning is immobilized on a small segment of the surface of a solid for each segment of individual probes (Nature Biotech 16, 27, 1998). The latter has the advantage that a peptide chip or DNA chip with the required probes can be made relatively easily, and is the method of choice of many startup companies.

SUMMARY OF THE INVENTION

A probe chip for biological materials, including DNA, is a highly anticipated to be used as a testing tool. However, for practical purposes, the following conditions have to be satisfied: (A) a small amount of a large variety of chips can be made at low cost, (B) a probe can be immobilized homogeneously, (C) data is highly reproducible and the chip is reusable, and (D) the chip can be heated to remove nonspecifically absorbed substances. However, problems remain: For example, (a) the probes are not consistent from one segment to another, (b) production is very labor-intensive, (c) very fine segmentation for immobilization is not possible, and (d) probes are not uniform; because (i) they are immobilized as liquid drops on the surface of a solid, and (ii) probes are positioned and immobilized simultaneously. Furthermore, (d) bind weakly with the surface of the solid and may dislodged upon heating, because (iii) many probe chips are immobilized by adsorption or the like.

In order to solve the aforementioned problems, immobilization of probes on the solid surface and alignment of the probes may be separated into two or more different steps to enable uniform DNA probes to be produced on the solid surface. The probes can be immobilized via covalent bonds, which are heat stable, therefore, nonspecifically absorbed substances can be appropriately removed by heating. Fine particles, used as the solid on which probes are immobilized, are aligned to produce a probe array having segments of a suitable size. Any desired probe array can be readily produced by exchanging the aligned fine particles with the probes. Tweezers can be used to align fine particles having a diameter of about 0.3 mm but this method would be difficult for particles having a diameter of less than 0.1 mm. Therefore, in an embodiment, the present invention provides a method and an apparatus to produce a probe array, in which fine particles each held in a fine hole on a sheet are transferred and aligned in a capillary, a groove on a plate or the like. In an alternative method, fine particles are controlled to flow as individual particles into a liquid for transfer into a capillary to produce a probe array. Furthermore, in order to improve reproducibility in measurement, a multiple number of fine particles with a multiple number of probes are aligned for each probe to check any variation in test results to obtain highly reliable data.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIG. 2 is a conceptual view of a detection system to measure a bead array with probes retained in a capillary or the like.

FIGS. 3a-3g are fragmentary sectional views of an apparatus for bead alignment. FIG. 3a is a conceptual view of bead feeding in an off-line state. FIG. 3b is a conceptual view in which a bead is trapped in a hole. FIG. 3c is a conceptual view in which a bead is moving into a capillary or the like. FIGS. 3d-3g show the subsequent steps.

FIG. 4a is a perspective illustration. FIG. 4b is a sectional view.

FIG. 5c is a cross-sectional partial view.

FIGS. 9a and 9b are conceptual views of a method of aligning probe beads using a sheet with holes.

FIG. 10a is a general view. FIG. 10b is a sectional view. FIG. 10c is a conceptual view for measurement.

DETAILED DESCRIPTION OF THE PREFERRED EMBODIMENT

Figure 1:
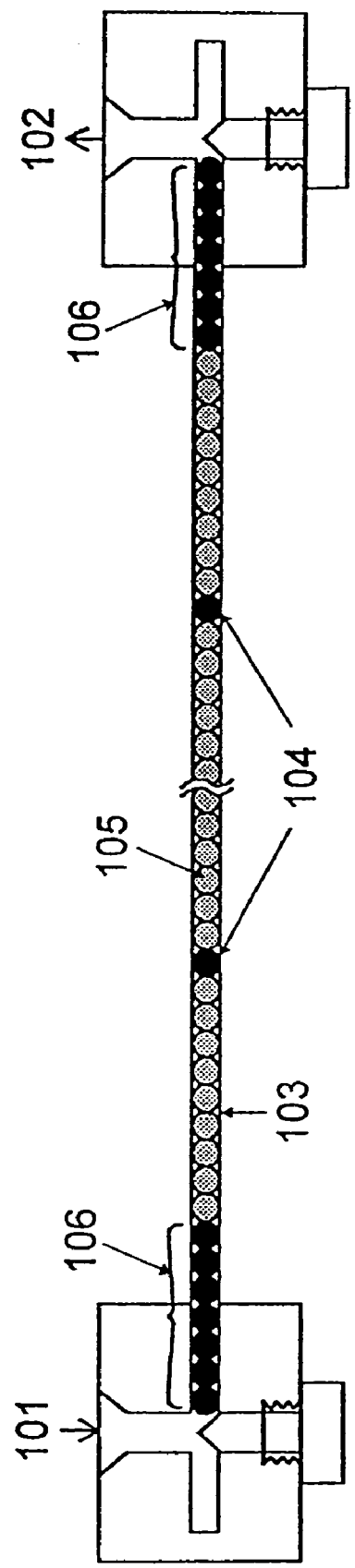
FIG. 1 is a conceptual view of a probe array chip comprising beads with probes aligned in a capillary.

The present invention includes a plurality of aspects and embodiments. In one aspect, a method for producing a probe array comprises the steps of: (a) selecting plural types of probes of interest; (b) immobilizing the plural types of probes on surfaces of different solid pieces, respectively; and (c) aligning the probe-immobilized solid pieces in a designated order to obtain a probe array for analyzing a sample solution passing therethrough. In the above, the probes may be polynucleotides, peptides, or proteins. In an embodiment, the solid pieces are beads which may be fine particles. Further, the alignment of the solid pieces may be a one-dimensional arrangement or a two-dimensional arrangement. In another embodiment, the method further comprises placing solid pieces as markers at specified intervals in the alignment. The markers may have a different size from that of the solid pieces with probes. In an embodiment, each solid piece has one type of probe immobilized thereon, and a designated number of solid pieces for each type of probe are prepared. Additionally, the alignment of solid pieces may be conducted in an array selected from the group consisting of a capillary, a groove, and an optical cell.

In an embodiment of the method, the alignment of solid pieces may be conducted by (i) placing the probe-immobilized solid pieces on a sheet having a hole through which one solid piece can pass, said sheet being placed on a movable base having a through-hole leading to the interior of the array, said movable base being positioned where the hole of the sheet does not communicate with the through-hole of the movable base; (ii) trapping one of the solid pieces in the hole of the sheet; (iii) removing the remaining solid pieces from the sheet; (iii) moving the movable base to a position where the hole of the sheet communicates with the through-hole of the movable base; (iv) transferring the trapped solid piece to the array via the through-hole; and (v) repeating steps (i) through (iv) until the probe-immobilized solid pieces are aligned in the designated order in the array. In another embodiment of the method, the alignment may be conducted by (i) placing the probe-immobilized solid pieces on a sheet having a hole through which one solid piece can pass, said hole leading to the interior of the array, said hole being closed with a valve; (ii) trapping one of the solid pieces in the hole of the sheet; (iii) opening the valve to transfer the trapped solid piece to the array, and (iv) repeating steps (i) through (iii) until the probe-immobilized solid pieces are aligned in the designated order in the capillary, groove, or optical cell.

In yet another embodiment of the method, the alignment may be conducted by (i) placing the probe-immobilized solid pieces in wells, each well containing a single type of probe-immobilized solid pieces, each well having a hole through which one solid piece can pass, said hole being closed; (ii) trapping one of the solid pieces in each hole of each well; (iii) opening and closing each hole after moving the wells in a designated order to transfer each trapped solid piece to an array; (iv) moving the wells to align the probe-immobilized solid pieces in a next array; and (v) repeating steps (i) through (iv) until a designated number of arrays are filled with the probe-immobilized solid pieces aligned therein.

In still another embodiment of the method, the alignment may be conducted by (i) placing the probe-immobilized solid pieces in a narrow tube; (ii) moving the solid pieces one by one with a solution flowing along the narrow tube, to transfer the solid piece to the array, and (iii) repeating steps (i) and (ii) until the probe-immobilized solid pieces are aligned in the designated order in the array.

Additionally, in an embodiment, the alignment may be conducted by (i) placing the probe-immobilized solid pieces in sections, each section containing a single type of probe-immobilized solid pieces, each section having a hole through which one solid piece can pass, said hole being closed; (ii) trapping one of the solid pieces in each hole of each section; (iii) opening and closing each hole after moving the sections in a designated order to transfer each trapped solid piece to a groove; (iv) repeating steps (i) through (iii) until the probe-immobilized solid pieces are aligned in the groove in order; and (v) transferring the aligned probe-immobilized solid pieces to an array wherein the solid pieces are placed close together.

In the above, each embodiment can exhibit at least one of the aforesaid advantageous effects.

The present invention can be applied to other aspects, including a probe array for analyzing a sample solution passing therethrough, and various apparatuses for manufacturing a probe array.

The present invention will be explained by the following examples. A probe array of the present invention can be commonly explained either with DNAs, proteins, peptides or other biological materials. Accordingly, DNAs are used for explanation in the following examples.

In a DNA probe array according to the present invention, solid probes are held either one-dimensionally in a capillary or two-dimensionally in a small area of an optical cell. The capillary is mainly used in the Examples for convenience of explanation. Round beads are used as the fine particles in the Examples but any particles having cubic or other shapes can be used. Beads having a diameter of 1-300 microns can be used; however, beads having a diameter of 20 microns are mainly used in the Examples. Further, glass or plastic beads are normally used; however, metal materials such as gold can also be used. Plastic beads are used here.

EXAMPLE 1

FIG. 1 shows an example of a probe array according to the present invention, wherein numeral 101 is an inlet for solution and sample, 102 is an outlet, 103 is a capillary for holding probe array, 104 are marker beads, 105 is a bead with probe, and 106 are dummy beads. The diameter of the beads with immobilized probes is 20 microns and the inner diameter of the capillary 103 is 25 microns. In this Example, about 20 dummy beads 106 are aligned on both ends and 999 beads 105 are aligned between them. Every $10^{th}$ bead is a black bead 104 and every $100^{th}$ bead is a red bead for a total of 99 marker beads and 900 probe beads, that is, 900 different kinds of probes can simultaneously be used for tests. These beads could be aligned in a 2 mm length if densely packed; however, in this example, for hybridization and other considerations, the beads were more loosely packed and held in a 5 mm length. The retention length can be longer or shorter than the above described range (e.g., in the range of 2-10 mm per 1000 beads). However, an excessively long length increases the amount of sample needed, while an excessively short length causes a problem in handling. Moreover, a sample may be not adequately hybridized. The volume of the reaction area is about 2.3 n liters. Stoppers are placed in both ends to prevent the beads from flowing-out. The sample and washing fluid are introduced and discharged through these ends via the inlet 101 and the outlet 102. The probe array is advantageously compact and easy to handle since as many as 10,000 probes can be held in an area of 20-30 mm in length.

Figure 2:
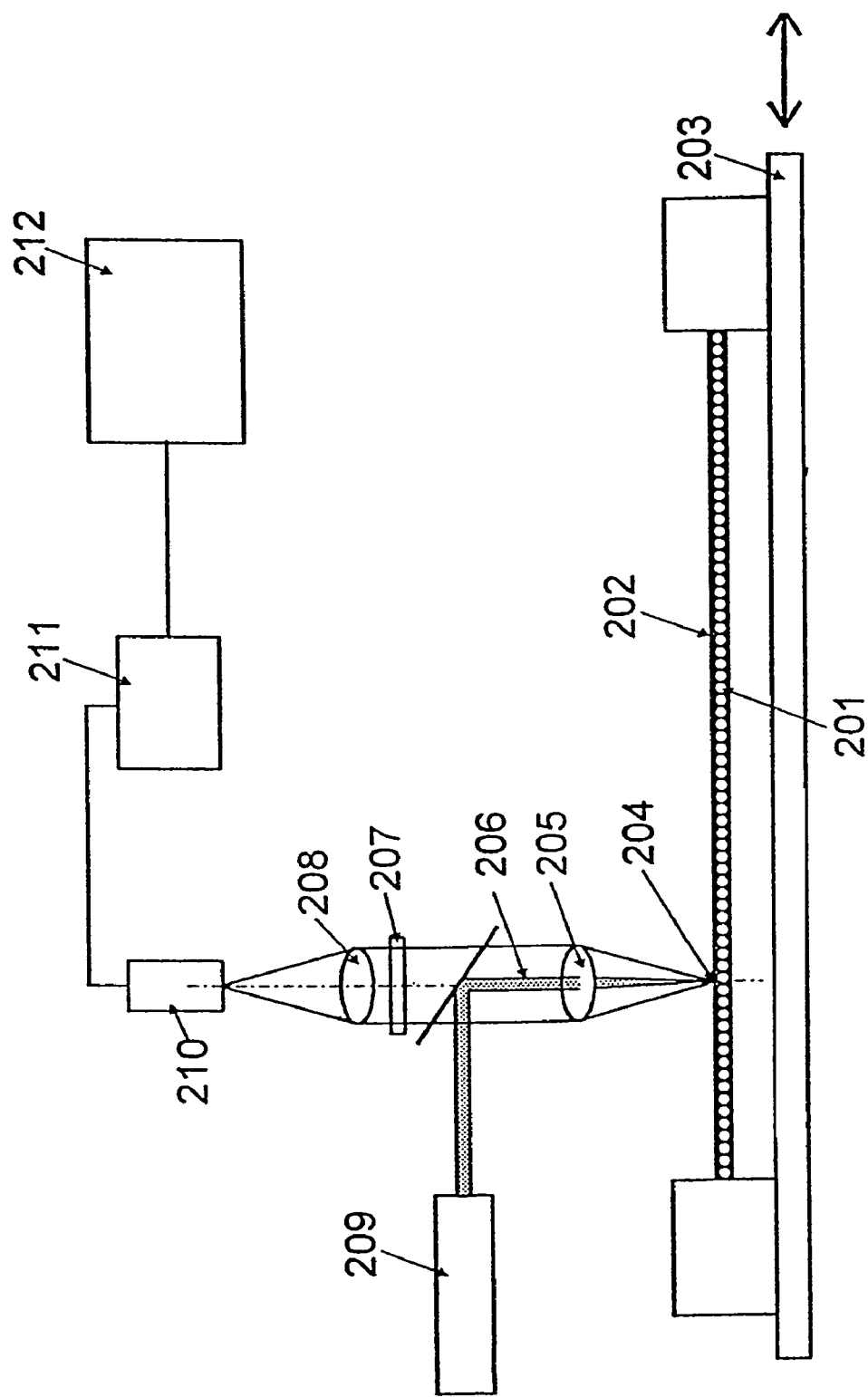

The irradiating laser beam 206 and the probe holding capillary 202 are relatively scanned and the resulting fluorescence is measured using a fluorescence detection device, for example, as shown in FIG. 2. In FIG. 2, numeral 201 is a bead with probe, 202 is a capillary for holding probe array, 203 is a plate to move probe array, 204 is a point of irradiation and emission, 205 is a lens, 206 is a irradiation laser beam, 207 is a optical filter, 208 is a lens, 209 is a laser source, 210 is a detector, 211 is a controller for data processing and detector, and 212 is a indicator. Different probes are readily identifiable by the aid of marker beads placed every 10 beads 201. Marker beads can be colored differently to identify different probes, or alternatively, each group of 10 beads with probes can be colored differently. Of course, in this case, colors would have to be chosen so as not to have a wavelength which would interfere with the fluorescence detection.

EXAMPLE 2

This Example relates to a method and an apparatus in which beads are aligned in a capillary one at a time in predetermined order. FIGS. 3a-3g show an example of a device to make the bead array. In these figures, numeral 301 is an outlet for solution and beads, 302 is an inlet for solution, 303 is a cover plate, 304 is a bead with probe, 305 is a hole for bead trapping, 306 is a capillary for bead alignment, 307 is a capillary holding base, 308 is a trapped bead, 309 is a nozzle for bead supply, and 310 is a stopper. For convenience of explanation, beads are aligned in one capillary in this Example; however, for practical use, a multiple number of holes on a sheet and a multiple number of capillaries are used. Step 1 (FIG. 3a): Beads with the first probe (probe bead #1, 304) are introduced with a solvent into the cell 303 having the sheet 311 with a hole at the bottom. The beads are precipitated and the solvent is moved back and forth and right and left to drop one of the beads 305 into the hole. Step 2 (FIG. 3b): The remaining beads are removed with the solvent 302 via the outlet 301 and washed. Only the bead which dropped into the hole remains in the cell. In this case, the solvent may be blown out of the port at a right angle to the sheet to remove these beads near the port and leave the one bead in the sheet hole to be introduced into the capillary in step 3. The bottom of the hole is closed off by the block 307. The capillary for the alignment of the beads is fixed to this block, but in steps 1 and 2, the axis 306 of the capillary and the hole are not aligned such that the bead 305 is retained in the hole. Step 3 (FIG. 3c): The block 307 and the sheet 311 are moved relative to each other to align the axis of the capillary and the hole. Probe bead #1 (305) is introduced into the capillary by suction from the other end or with pressure applied from the solution injection side. In this case, the relative movement of the block and the sheet is about the same order as the diameter of the hole, for which a piezoelectric element is successfully used. Step 4 (FIG. 3d): The block 307 and the sheet 311 are relatively moved so that the axis 306 of the capillary and the hole 308 are again out of alignment. Step 5 (FIG. 3e): Beads with the second probe (probe bead #2, 320) are introduced into the cell 303 and one of them 321 is dropped into the hole. Step 6 (FIG. 3f): Excess beads other than the bead in the hole are removed from the cell in the same manner as in step 2. Step 7 (FIG. 3g): The block and the sheet are moved relatively to align the axis of the capillary and the hole such that the probe bead #2 (321) can be introduced into the capillary. As a result, the bead with probe 1 (probe bead 1) and the bead with probe 2 (probe bead 2) are aligned in the capillary. By repeating these steps, a bead array with probes having a desired order can be produced.

Figure 4A:
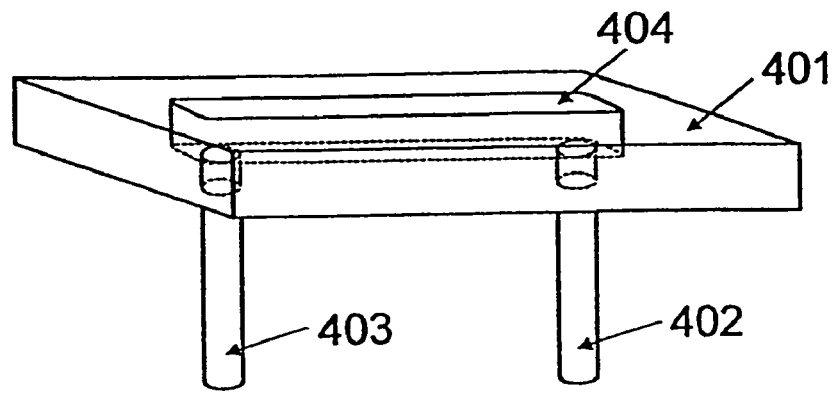
FIGS. 4a and 4b are conceptual views of an apparatus for the groove-type bead alignment.
Figure 4B:
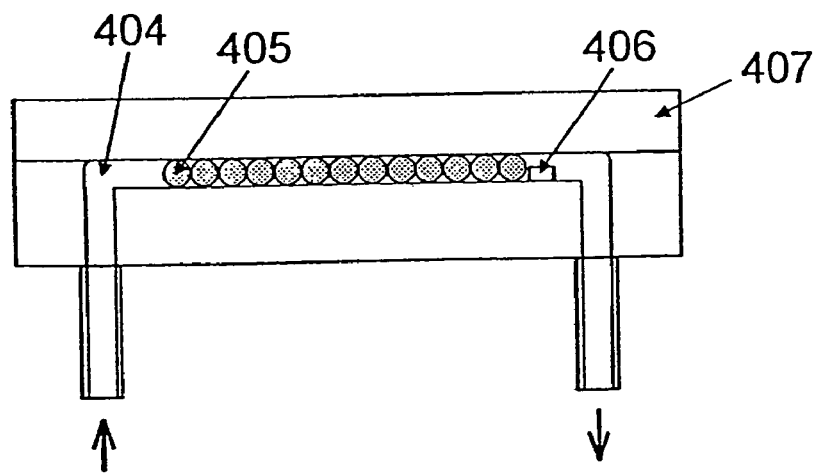

The capillary used here can be taken out and used as a probe array holder during measurement, or a probe array holder can be made separately and attached to the bottom part of the capillary to which the bead array is transferred. In this Example, the probe array holder shown in FIGS. 4a and 4b is used. In these figures, numeral 401 is a base with a bead array holding groove, 402 is a solution outlet capillary, 403 is an inlet for beads and various solutions, 404 is a groove for bead alignment, 405 is a bead with probe, 406 is a stopper, and 407 is an upper window. A sample solution is injected from the left side (403) of the Figure. After sufficient hybridization, a washing liquid is injected from the right side (402) to remove the unreacted sample portion. After mounting the probe array holder onto a measuring unit, each bead is irradiated with a laser beam and emitted fluorescence is detected. Of course, instead of emitted fluorescence from laser beam irradiation, emitted light produced by a chemical emitting reagent can also be detected. Any detection method which can detect the presence and absence of hybridization can be used.

In this Example, the invention is explained with only one capillary fixed to the block; however, it is possible to produce a large number of probe arrays simultaneously using a multiple number of capillaries. In that case, it is naturally understood that the number of holes on the sheet has to be increased as the number of capillaries increases.

EXAMPLE 3

Figure 5A:
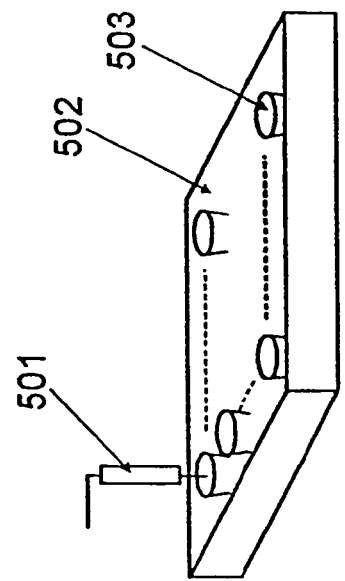
FIGS. 5a, 5b, and 5c are conceptual views of a method for producing a bead array using grooves and a movable valve.
Figure 5B:
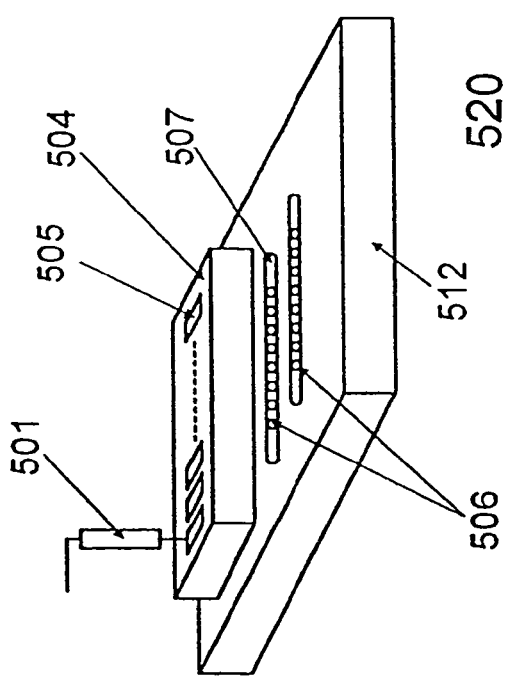
Figure 5C:
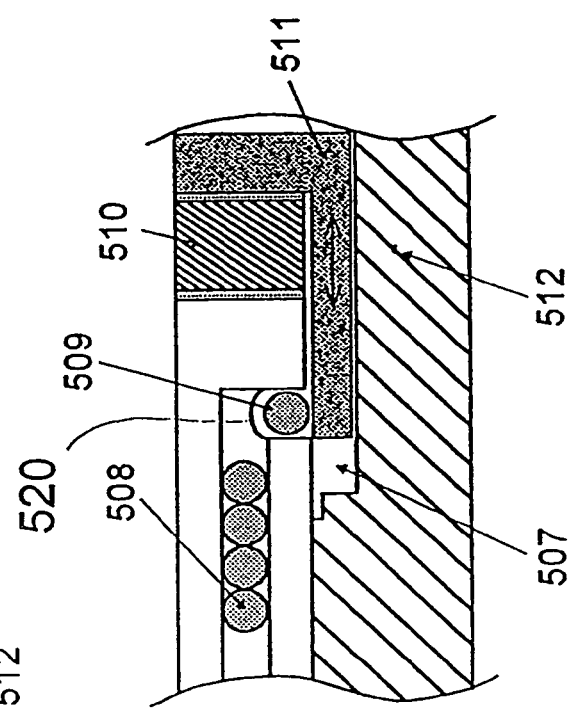

This example is for an apparatus in which a bead delivery device 504 having holes (or wells) to keep various kinds of beads separately to transfer them to a bead arraying plate 512 having grooves 507 on it or a capillary for aligning the beads according to the predetermined order as a probe bead array. At first solutions containing different kinds of probe beads placed in wells of a titer plate are transferred one after another in a predetermined order into designated wells (holes) of a bead delivery device such that the beads are aligned in a groove produced in a plate or a capillary (FIGS. 5a, 5b, and 5c). In these figures, numeral 501 is a pipetter/injector, 502 is a titer plate which has wells 503 containing probe beads, 504 is a bead delivery device with holes, 505 is a hole which holds probe beads being delivered to a groove, 506 are arrayed probe beads, 507 is a groove in which various kinds of probe beads are aligned, 508 is a probe bead, 509 is a probe bead trapped in a hole, 510 is a piezoelectric element, 511 is a movable valve, and 512 is a holding base. The beads are suctioned from the wells in the titer plate 502 with the pipetter 501 and moved into a transfer well 505. The hole 520 for trapping a bead is open at the bottom of the well. One of the beads 509 (a multiple number of the beads if a multiple number of the holes are provided) injected into the well 505 drops into the hole 520, and the presence of the dropped bead is optically confirmed. Then, excess beads are recovered or removed from the well by flushing beads out with washing liquid. The valve 511 which can be driven by a piezoelectric element 510 or the like is placed between the bead trapping hole 520 and the groove 507 or the capillary. A bead can be transferred to the groove or capillary side by moving the valve. Actual bead movement is controlled by a liquid flow. Of course, the bead can also be transferred by moving the plate 504 to align the hole and the groove or the center of the capillary. Once the bead is fully transferred, the valve is moved back or the relative position of the hole and the capillary is shifted so that the bead is trapped in the hole. Beads with the next probe are introduced into the trapping site using a pipetter. The steps above are repeated to produce a bead array. The resulting bead array 506 is used as it is, or transferred to another container while maintaining the alignment and used as a probe array.

The steps above can be carried out in a system having a multiple number of holes to save time in array production, or to simultaneously produce a multiple number of the same arrays.

EXAMPLE 4

Figure 6:
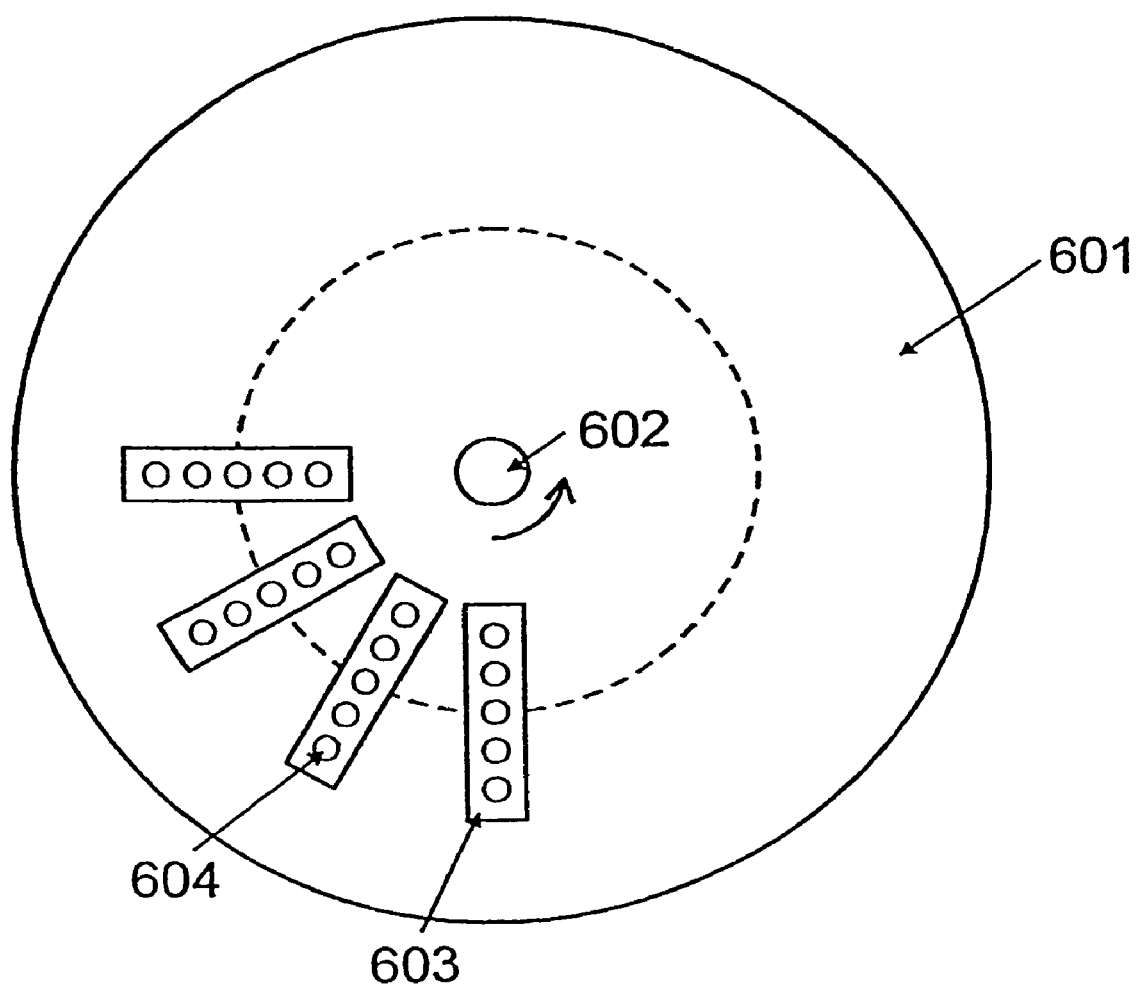
FIG. 6 is a conceptual view of a disk-type system for probe bead transfer.

In Example 2, one kind of probe bead at a time is aligned using a bead delivery device with one hole. In this example, a multiple number of wells in a bead delivery device are used to segmentally hold multiple kinds of probes bead in order to improve productivity. As shown in FIG. 6, a multiple number of rectangular wells 603 are placed on a rotary disk 601. In FIG. 6, numeral 601 is a disk-type bead holding plate for delivering beads, 602 is a rotary axis, 603 is a groove for bead holding, and 604 is a hole for bead holding. The bottom of each well is fitted with a sheet with holes as described in Example 1 at the bottom. The lower part of the rotary disk having the sheets has contact with a block, which holds capillaries, to prevent dropping of the beads trapped in the holes. When the rotary disk is moved and the holes and the axis of the capillaries are aligned, the probe beads are transferred into the capillaries in the same manner as described in Example above. The number of the holes corresponds to the number of the capillaries. The holes and the capillaries are correspondingly positioned; however, in order to prevent shearing upon rotation, a controlling mechanism is provided, in which the block with capillaries is moved in the axial 602 direction of the disk using a tracking technique similar to that used for CD-ROMs. In this example, a rotating board having a diameter of 16 cm is used. Wells 603 (1 mm wide and 30 mm long) are located at a position 5 cm from the axis of the disk. The pitch of the wells is 2 mm and about 150 wells can be radially placed on the disk. The sheet with holes is spread under the wells and the pitch of the holes is 2 mm. In this example, a total of 10 holes are aligned so that probe bead arrays can be made in 10 capillaries. Of course, the number of capillaries and the number of probe arrays producible at one time can be changed as required.

The rotary plate rotates in two rotation modes; a high speed rotation mode and a low speed but highly accurate mode. Beads are introduced into the well with a solution. The beads are dropped into the holes by moving the disk and flowing the solution out of the holes. Next, excess beads are moved to bead holders located on the end of the wells by centrifugal force and by water flow by rotating the disk in the high speed rotating mode. The disk is stopped, then, disk rotation is set to the highly accurate mode so that the capillaries and the probe beads #1 align. A shutter at the bottom of the disk is opened and the block which is holding the capillaries is brought into contact with the rotary plate such that the wells carrying probe bead #2 are moved to the position of the capillaries. The beads are sequentially transferred into capillaries to produce probe bead arrays in a designated order. A large number of probe beads can be aligned and held in capillaries by exchanging the disk or the probe beads to be placed in the wells and repeating the above described steps. The position of a specific probe in a resulting probe bead array can be conveniently confirmed by changing the color of beads in the arrays every 10 beads.

EXAMPLE 5

Figure 7:
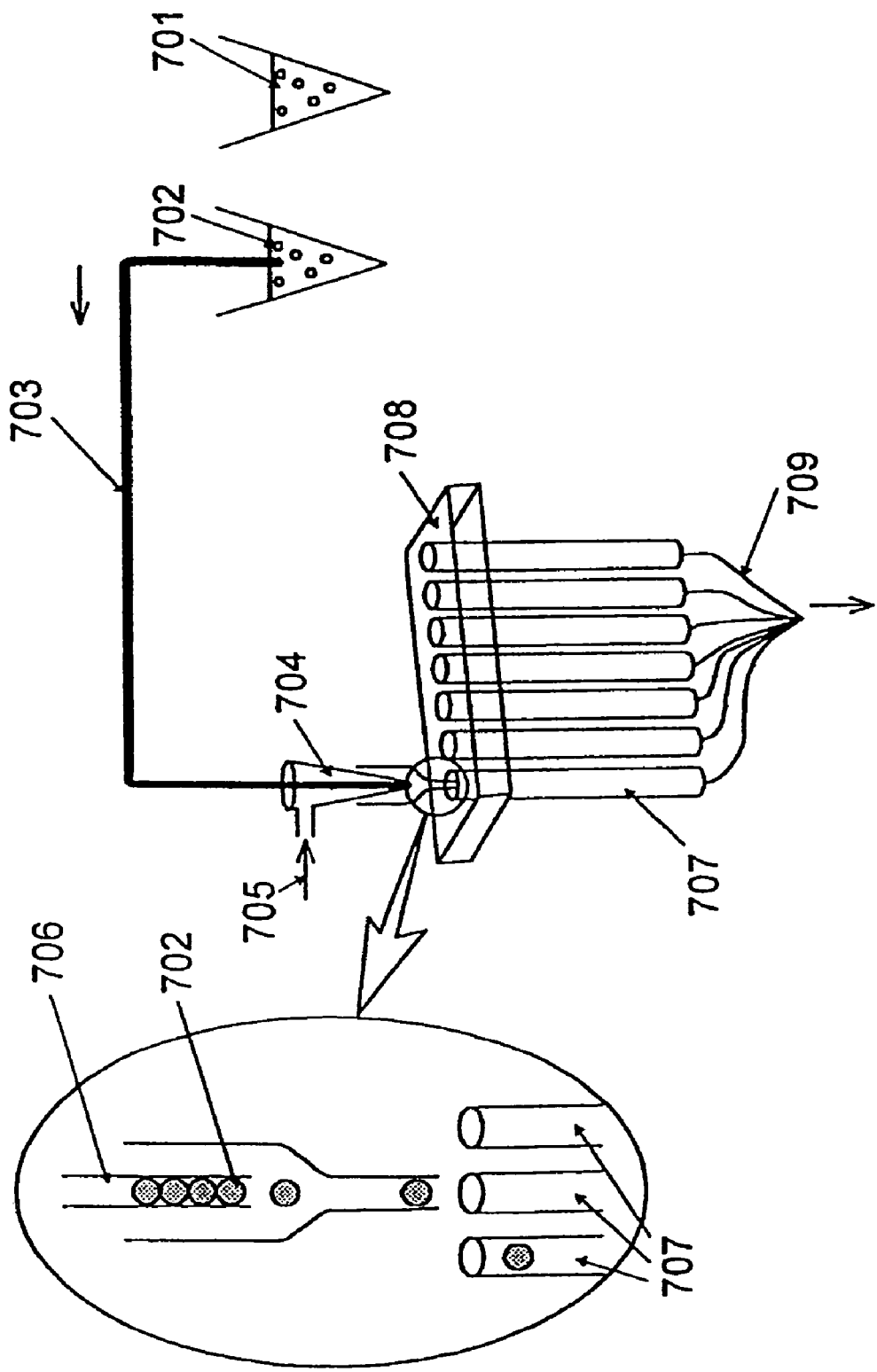
FIG. 7 is a conceptual view of a liquid flow-type bead array production method.

This example relates to a method and an apparatus for the alignment of probe beads into a capillary one by one in a designated order using a liquid flow. FIG. 7 shows a conceptual view of this example. In this figure, numeral 701 is a bead solution reservoir, 702 is a bead with probe, 703 is a transfer tube, 704 is a sheath flow cell, 705 is a transfer liquid, 706 is a capillary tube for transfer, 707 is a capillary for bead array alignment; 708 is a supporting base, and 709 is a solution outlet tube. Beads 702 with probes are pumped into the transfer capillary tube 707. The end of the capillary tube is inserted into a liquid flow formed with the transfer liquid 705 in the sheath flow cell 704, and the beads are released into the liquid flow one by one, and virtually constant intervals. However, to stabilize the release, ultrasonic waves are applied to that portion of the capillary holding the beads to form knots along the axis of the capillary. The beads are released one by one into the liquid flow at designated intervals by controlling conditions such as the intensity of the ultrasonic waves.

EXAMPLE 6

Figure 8:
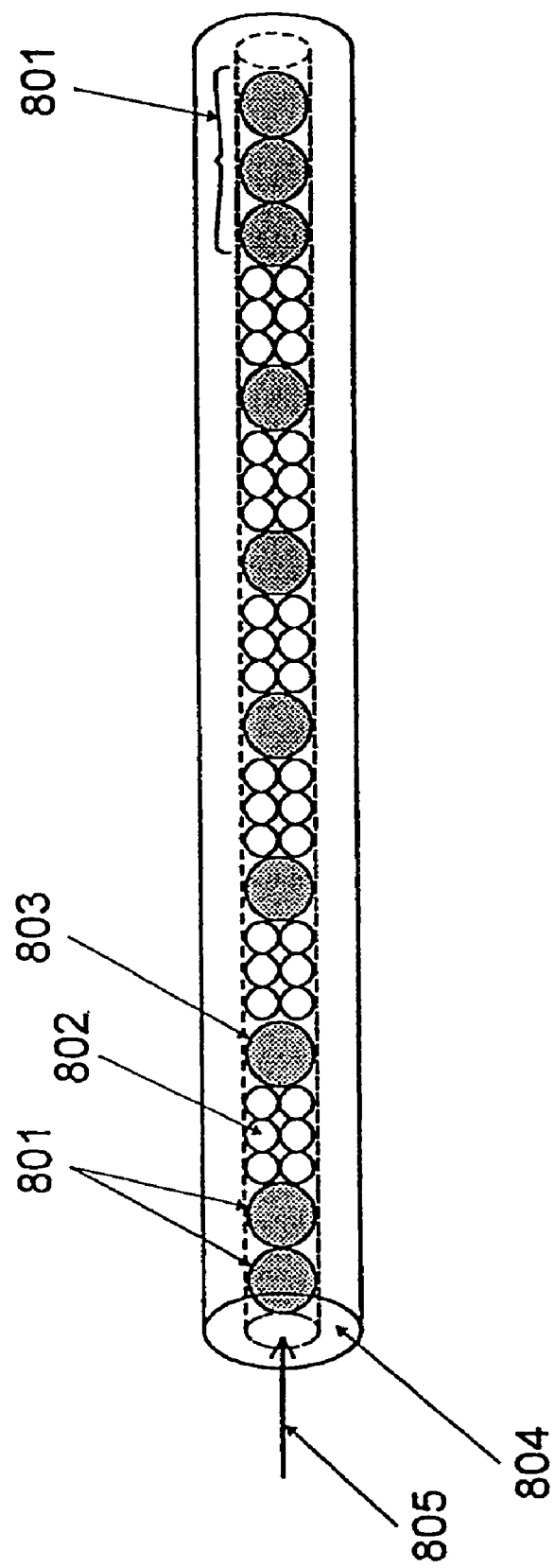
FIG. 8 is a conceptual view of a bead array in which a large number of beads are separated with marker beads.

In the examples above, one bead corresponds to one kind of probe. However, in order to check uniformity of hybridization reactions or to improve detection sensitivity, it is appropriate to use a multiple number of beads for one kind of probe. It is not necessary that the same number of beads be used for all probes. If the number varies held in a capillary for making a probe array, however, colored beads or beads of a different size have to be inserted between bead groups with different probes as markers. This example is shown in FIG. 8. In this figure, numeral 801 is a large size dummy beads, 802 is a probe bead, 803 is a large size marker bead, 804 is a capillary for probe holding, and 805 is a sample flow path. The apparatus for the production is virtually the same as described above, except that the size of the holes is several times larger than the size of the beads 802 so that a multiple number of beads 802 are trapped in the holes. Subsequent procedures are the same as described above.

Further, the bead array of this example can be easily produced if the liquid flow system described in Example 5 is used. A small number of beads are suctioned from a bead reservoir with a pipet and injected into the liquid flow. Although the number cannot be confirmed, the injected beads can be sequentially placed into the capillary 804. Prior to the injection of another kind of beads, a colored bead or a bead of a different size (801) is injected as a marker so that the position and the kind of probe of individual beads can be identified.

EXAMPLE 7

The previous example is a method for the production of a probe array in which probe beads are aligned in a capillary. This example as shown in FIGS. 9a and 9b discloses a method and an apparatus in which beads are first aligned in a groove produced on a plane surface, then congregated into a probe array or transferred into a capillary to produce a probe array. In FIGS. 9a and 9b, numeral 901 is a plate having wells, 902 is a well for a bead reservoir, 903 is a bead holding hole, 904 is a sheet with holes and is usually attached to the plate 901, 905 is a base array production holder with grooves for aligning beads, 906 is a fine groove for probe bead alignment, 907 is a bead with probe, and 908 is a capillary for bead array. First, a bead array production holder 905 having a multiple number of grooves 906 on a plane surface is prepared. Beads 907 with probes are aligned in each groove and transferred into a capillary 908 or the like while maintaining their alignment, then the beads aligned in the multiple number of grooves are introduced into different capillaries and used as a probe array. A plate attached with a sheet having holes (901, 904) is placed on top of the bead array production holder wherein beads are trapped in the holes and transferred into the above described grooves. As shown in FIG. 9, this plate with a sheet has wells (bead reservoirs 902) orthogonal to the grooves on the beads array production holder, and the holes 903 holding beads are through holes and opened for the fine groove. The apparatus does have a multiple number of grooves, but beads with different probes are injected into different wells in the plate and held in different holes. The plate attached with a sheet and the plate having grooves are used in close contact but can slide each other. At the start, the holes 903 of the sheet and the grooves 906 for the bead array production holder are not aligned. Beads with probes are supplied into different wells 902 of the plate above the sheet with holes for each kind of probe. One bead drops into one hole and retained there because the bottom of the hole is closed at this state. When the holes of the sheet and the grooves of the bead array production holder are aligned, the beads drop one by one from individual holes into the grooves 906. Since different probe beads drop into one groove from different positions, a variety of probe beads are retained in a groove. The beads are placed virtually at the same intervals as those in the bead reservoir 902 on the sheet with holes. In this example, the interval is 2 mm. A total of 50 beads are dropped into each groove of the bead array production holder in this example. Also, 10 bead arrays can be simultaneously produced in this example, but the number can be increased as desired. After dropping the beads, the positions of the sheet with holes 903 and the grooves 906 of the bead array production holder are shifted to seal up the grooves, after which the beads are introduced into the capillary 908 with a liquid flow. The number of different kinds of probes can be arrayed by repeating the above described steps.

In this example, a one-dimensionally aligned probe bead array is disclosed; however, naturally, probe arrays having many more kinds of probes can be produced by arranging a multiple number of these arrays or by two-dimensionally aligning these arrays.

EXAMPLE 8

Figure 10A:
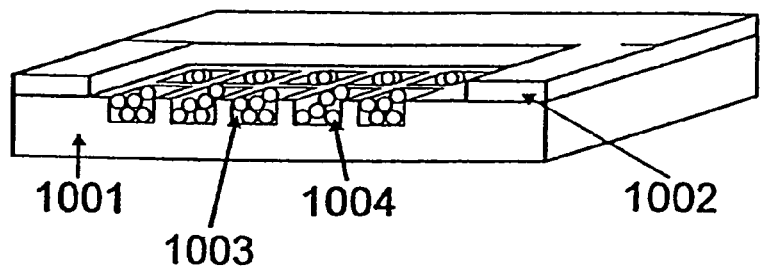
FIGS. 10a, 10b, and 10c are conceptual views of a microtiter plate-type bead array holder.
Figure 10B:
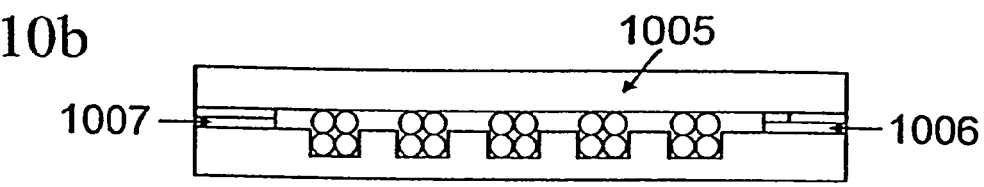
Figure 10C:
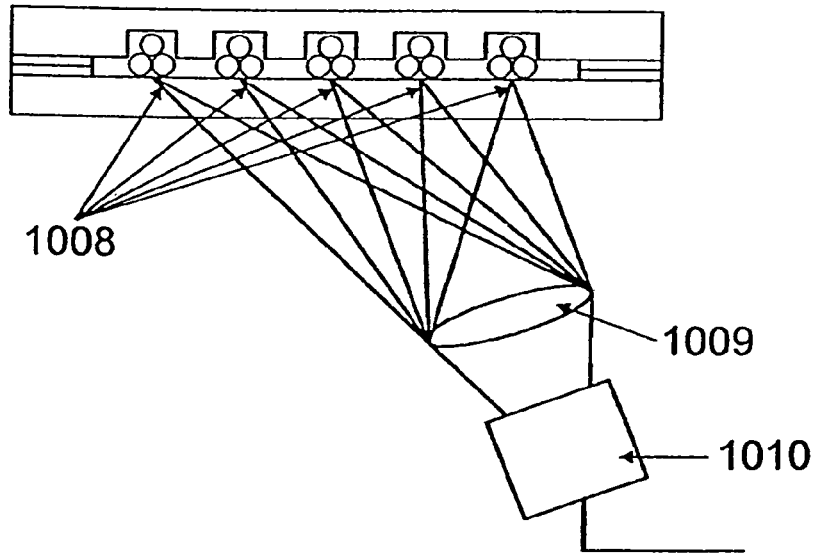

In this example, a probe bead array holder comprises cells which consist of a plate with one-dimensionally or two-dimensionally distributed holes and a cover glass. In FIGS. 10a, 10b, and 10c, numeral 1001 is a microtiter plate-type bead array holder, 1002 is a spacer, 1003 is hole which makes a bead array cell with a cover glass, 1004 is a bead with probe, 1005 is a cover glass, 1006 is a solution outlet, 1007 is a solution inlet, 1008 is a laser beam, 1009 is a lens, and 1010 is a detector. This resembles a micro titer plate. A small number of beads are suctioned from a titer plate in which probe beads are held, and dispensed into holes (cells) 1003 of the plate 1001. The beads 1004 are dispensed into the holes at designated positions according to the kind of probe to produce a microtiter plate-type bead array with probe beads. After the beads are dispensed, the cover glass 1005 which is optically transparent and does not interfere with the measurement of fluorescence or chemical emission is placed on top to produce a cell array. The space between the cover glass and walls, which segment the cells of the microtiter plate-type cell array, is smaller than the size of the beads so that the beads cannot move out. The reaction solution or the like can flow through the cells freely. For use, the cells are turned upside down to make the glass side down. In this case, the beads on the glass surface are sufficiently in contact with the reaction solution independent of the depth of the cells and the probes undergo hybridization with the target.

Effectiveness of the Invention

As described above, according to the present invention, a large number of probe arrays for peptides or DNAs can be produced by a simple procedure. The process to immobilize probes on the surface of a solid and the process to align probes are separated, so that both processes can be optimized. As a result, immobilized probes which are homogeneous and not easily removable from the surface of the solid can be produced, then an array having the required kinds of probes can be readily produced by aligning the beads in a designated order. Also, a fine probe array, which is difficult to make by a conventional method, can be produced by reducing the size of the beads. A probe array with new components can be produced simply by preparing the required DNA probes, immobilizing them on the surface of beads and setting the probe beads onto a production apparatus, and thus arrays as requested by users can be provided any time. By aligning a multiple number of beads carrying the same probes, statistical averages can be obtained to analyze reproducibility and quantitativeness, and reliable measurements can be carried out. Furthermore, the reaction is quick and highly sensitive because the surface area for the reaction is larger than that in conventional DNA chips or the like being retained on a plane. The size of the beads can vary between 1 micron to 300 microns so that high density probe arrays can be readily produced if necessary. For example, by using 6-micron beads, 1,500 probes can be aligned in a 10-mm length in a capillary, or more than 1,000,000 probes can be retained in an area of 1 $cm^2$ if a two-dimensional probe array holder is used.

A multiple number of arrays having the same probe alignment can be produced by an extremely simple procedure and thus the arrays are also suitable for mass production.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A probe array having two ends comprising:
   plural types of probes immobilized on solid pieces, and
   a plurality of markers,
       wherein the solid pieces with probes immobilized thereon are aligned in a capillary in a designated order according to the type of probe,
       wherein the markers are colored solid pieces set at specified intervals in the designated order in the capillary such that different types of probes can be visually identified,
       wherein all probes between any two markers are identical and the color of the markers will not interfere with fluorescence, and
       wherein a dummy bead is placed at each end of the probe array.

2. The probe array of claim 1, wherein each solid piece with a probe immobilized thereon has one type of probe immobilized thereon, and wherein a designated number of solid pieces with probes immobilized thereon are prepared for each type of probe.

3. The probe array of claim 1, wherein the markers are of different size than the solid pieces with probes immobilized thereon.

4. The probe array of claim 1, wherein multiple solid pieces with probes immobilized thereon have the same type of probe immobilized thereon, wherein the number of solid pieces with probes immobilized thereon is different for different probe types.

5. The probe array of claim 1, wherein the solid pieces with probes immobilized thereon are colored.

6. The probe array of claim 5, wherein the colors of the solid pieces with probes immobilized thereon are selected so as not to interfere with fluorescence detection.

7. The probe array of claim 5, wherein all solid pieces with probes immobilized thereon between any two markers have identical probes immobilized thereon and define a group, wherein all solid pieces in a group are colored the same and solid pieces in adjacent groups are colored differently.

8. The probe array of claim 1, wherein one or more dummy beads are placed at each end of the probe array, multiple solid pieces with probes immobilized thereon have the same type of probe immobilized thereon, the solid pieces with probes immobilized thereon are colored, and the color of the markers and the colors of the solid pieces with probes immobilized thereon are selected so as not to interfere with fluorescence detection.

9. The probe array of claim 1, wherein the size of the dummy beads is bigger than the size of the solid pieces with probes immobilized thereon.

10. The probe array of claim 1, wherein a plurality of dummy beads are placed at each of the ends of the array.

* * * * *